United States Patent [19]

Knapp, Jr. et al.

[11] Patent Number: 4,764,358

[45] Date of Patent: Aug. 16, 1988

[54] RADIOLABELED DIMETHYL BRANCHED LONG CHAIN FATTY ACID FOR HEART IMAGING

[75] Inventors: Furn F. Knapp, Jr., Oak Ridge; Mark M. Goodman, Knoxville, both of Tenn.; Gilbert Kirsch, Woippy, France

[73] Assignee: The United States of America as represented by the United States Department of Energy, Washington, D.C.

[21] Appl. No.: 868,480

[22] Filed: May 30, 1986

Related U.S. Application Data

[63] Continuation-in-part of Ser. No. 728,975, Apr. 30, 1985, abandoned.

[51] Int. Cl.[4] .................... A61K 49/02; A61K 43/00; C11C 3/00
[52] U.S. Cl. ..................................... 424/1.1; 260/408
[58] Field of Search ..................... 424/1.1, 9; 562/598, 562/602, 606, 496, 493; 260/413, 408

[56] References Cited

U.S. PATENT DOCUMENTS

| | | | |
|---|---|---|---|
| 4,290,965 | 9/1981 | Stocklin et al. | 424/1.1 |
| 4,323,547 | 4/1982 | Knust et al. | 424/1.1 |
| 4,450,149 | 5/1984 | Kabalka | 424/1.1 |
| 4,473,544 | 9/1984 | Machulla et al. | 424/1.1 |
| 4,476,106 | 10/1984 | Bardy et al. | 424/1.1 |
| 4,523,033 | 6/1985 | Knapp, Jr. et al. | 562/496 |
| 4,524,059 | 6/1985 | Elmaleh et al. | 424/1.1 |

OTHER PUBLICATIONS

Otto et al, J. Labelled Compounds & Radiopharmaceuticals, XIX, Nos. 11–12, 1312–1313, 1982.
Knapp et al, Presented at the Proceedings of the International Symposium of the Developing Role of Short-Lived Radionuclides in Nuclear Medical Practice, Wash. D.C., May 1982.
Goodman et al, Presented at the 5th International Symposium on Radio Pharmaceutical Chemistry, Japan, Jun. 1984.
"Synthesis and Evaluation of Radioiodinated Terminal p-Iodophenyl-Substituted Alpha and Beta Methyl Branched Fatty Acids"; M. M. Goodman et al, J. Med. Chem. 1984, 27, 390–397.
"Regional Myocardial Substrate Uptake in Hypertensive Rats: A Quantitative Autoradiographic Measurement"; Yoshiharu Yonekura et al; Science; Mar. 22, 1985, pp. 1494–1496.
"Synthesis of 15-(p-Iodophenyl)-6telluapentadecanoic Acid: A New Myocardial Imaging Agent"; M. M. Goodman et al; J. Org. Chem., 1982, 47, pp. 3004–3006.
"New Myocardial Imaging Agents: Synthesis of 15(p-Iodophenyl)-3(R,S)-methylpentadecanoic Acid by Decompoition of a 3,3-(1,5-Pentanediyl)-triazene Precursor"; M. M. Goodman et al, J. Org. Chem., 1984, 49, pp. 2322–2325.
"The Design and Biologicak Properties of Iodine–123 Labeled beta–Methyl Branched Fatty Acids"; Furn F. Knapp et al; European Heart Journal, vol. 14 (1985)6(Supplement B), pp. 71–83.
"Radioiodinated 15(p-Iodophenyl)-3,3-Dimethylpentadecanoic Acid: A Useful New Agent to Evaluate Myocardial Fatty Acid Uptake" Furn F. Knapp et al; J. Nucl. Med. 27, No. 4, pp. 521–531, Apr. 1986.

Primary Examiner—John F. Terapane
Assistant Examiner—J. E. Thomas
Attorney, Agent, or Firm—Katherine P. Lovingood; Stephen D. Hamel; Judson R. Hightower

[57] ABSTRACT

A radiolabeled long chain fatty acid for heart imaging that has dimethyl branching at one of the carbons of the chain which inhibits the extent to which oxidation can occur. The closer to the carboxyl the branching is positioned, the more limited the oxidation, thereby resulting in prolonged retention of the radiolabeled compound in the heart.

2 Claims, 2 Drawing Sheets

RADIOLABELED DIMETHYL BRANCHED LONG CHAIN FATTY ACID FOR HEART IMAGING

This invention was developed pursuant to a contract with the U.S. Department of Energy.

BACKGROUND OF THE INVENTION

This invention is a continuation-in-part of previously filed copending application Ser. No. 728,975 filed 4/30/85 now abandoned. It relates to a radiolabeled dimethyl branched long chain fatty acid that is useful as a heart imaging agent.

The major energy requirements of the normal myocardium are met by the metabolic oxidation of long chain fatty acids. Regional differences in myocardial uptake of radiolabeled fatty acids could reflect not only differences in regional perfusion, but could also potentially be an accurate and elegant means of detecting subtle differences in regional metabolism. These agents could be uniquely used to evaluate by noninvasive methods various aspects of regional fatty acid metabolism in relation to heart disease and thus aid in diagnosis, prognosis and management of the cardiac patient.

A class of compounds being developed for heart imaging, radioiodine labeled long chain fatty acids, have presented problems. Instability of iodine-carbon bonds causes radioiodine to appear in the blood as well as the heart, and breakdown of the long carbon chain of the fatty acid results in rapid washout of the label from the heart, both problems making distinct imaging impossible. One approach to the development of a suitable radioiodine labeled fatty acid analogue has involved the stabilization of a radioiodine by attachment to the para position of the terminal phenyl ring of a long chain fatty acid. Another stabilization technique was to attach the radioiodine to a vinyl functional group on the chain. These stablization techniques were effective in inhibiting deiodination but there was still a problem with rapid washout of the labeled compound from the heart. To address this problem attempts were made to modify the fatty acid so that it would remain intact and not wash out of the heart after uptake. It was believed that oxidation of the straight chain fatty acid at the beta carbon was responsible for the lack of retention of the fatty acid in the heart; therefore there were attempts to inhibit this oxidation by placing a methyl group at the beta carbon. If theory was correct, this substitution should have inhibited the reaction that leads to degradation of the fatty acid thus resulting in indefinite retention of the radiolabeled compound in the heart. Although there was improved retention of the monomethyl branched compound when compared with the unbranched analogue, it was not as pronounced as would be expected from a compound that is essentially trapped in the heart with no avenue for degradation and washout.

SUMMARY OF THE INVENTION

In view of the above needs it is an object of this invention to provide a radiolabeled long chain fatty acid for heart imaging that exhibits prolonged retention.

It is another object of this invention to provide a radiolabeled long chain fatty acid for heart imaging that is radiolabeled with a gamma emitting radioisotope that has a sufficiently long half-life for its intended use.

Another object of this invention is to provide a radiolabeled long chain fatty acid that exhibits rapid uptake in the heart, indefinite retention, and high heart to blood ratios.

A final object is to provide a radiolabeled long chain fatty acid that does not undergo sequential alpha or beta oxidation. Other objects and advantages will become apparent to persons skilled in the art upon study of the specifications and the appended claims.

The invention is a compound that is a radiolabeled long chain fatty acid that is dimethyl branched. The dimethyl branching should be as close to the alpha carbon as possible. The preferred radiolabel is a radioiodine that is stablized on the chain by attaching it to a stabilizing moiety such as vinyl or phenyl. The preferred fatty acid is one containing from 10 to 21 carbons. The compound that the inventors developed and have successfully tested is 15-(p-iodophenyl)3,3-dimethylpentadecanoic acid, herein referred to as DMIPP. The invention is also a myocardial imaging agent comprising a compound of the invention and a physiologically compatible carrier medium which is suitable for intravenous injection.

DETAILED DESCRIPTION OF THE PREFERRED EMBODIMENT

Figure 1:
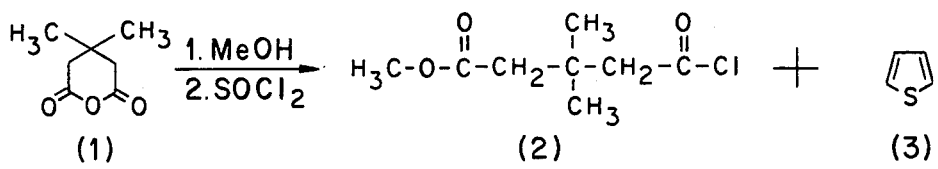
FIG. 1 is a diagram detailing the synthesis of 15-(p-iodophenyl)-3,3-dimethylpentadecanoic acid (DMIPP).
Figure 1:
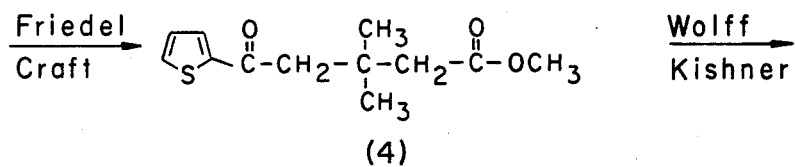
Figure 1:
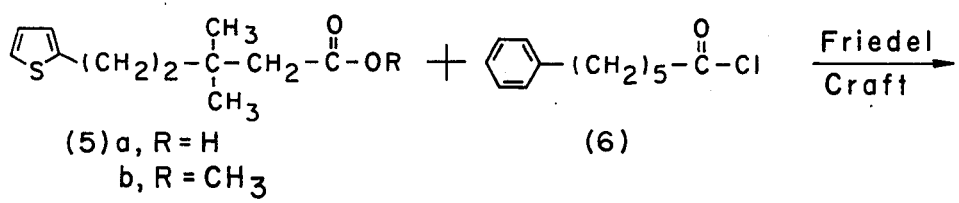
Figure 1:
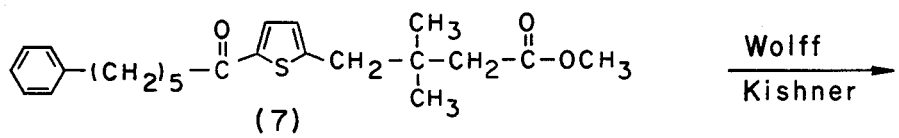
Figure 1:
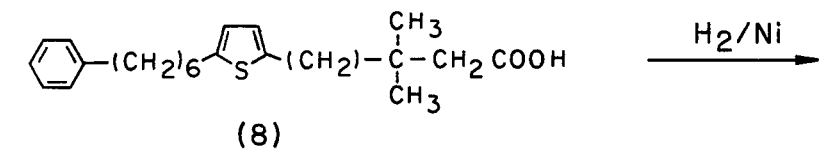
Figure 1:
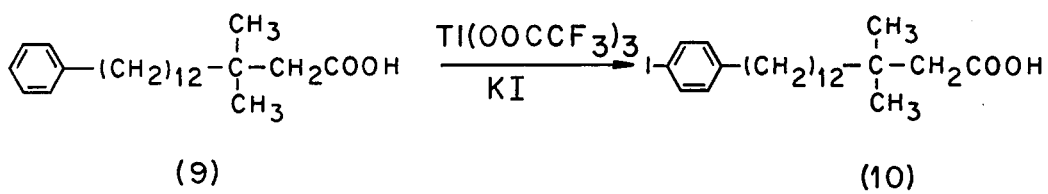

Since it was believed that long straight chain fatty acids showed rapid washout from the heart because of beta oxidation, early studies of labeled fatty scids for heart imaging concentrated on inhibiting beta oxidation. This was done by positioning a methyl group at either the alpha or beta carbon. Theoretically beta oxidation follows a reaction path shown in Equations 1 through 4. "R" represents a long chain to which is attached a radiolabeled tag.

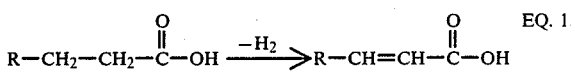

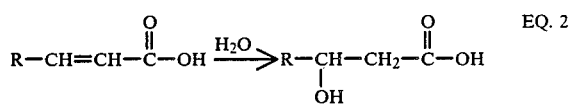

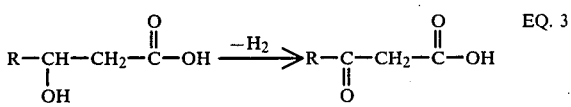

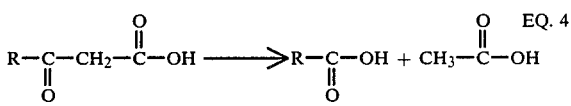

During in vivo oxidation the first step is oxidation, or loss of hydrogens from the alpha and beta carbons (EQ. 1), followed by hydration resulting in a hydroxyl group at the beta carbon (EQ. 2). A second oxidation at the beta carbon (beta oxidation) produces a ketone (EQ. 3) that degrades to acetic acid and another fatty acid (EQ. 4) which is oxidized again and spontaneously follows the same reaction path as the long chain fatty acid of Equation 1. A series of these reactions rapidly results in the washout of the radiolabel from the heart.

The theory of the inventors was that if a methyl group were placed on the chain at the beta position, beta oxidation would be inhibited as shown in Equations 5 and 6.

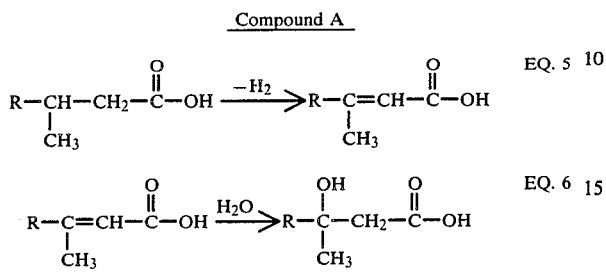

Oxidation again occurs at the alpha and beta carbons (EQ. 5) followed by hydration (EQ. 6), but this time beta oxidation cannot occur because there is a methyl group present at the beta carbon instead of a hydrogen which is needed. If this theory were correct then the reaction would stop at this point and the labeled compound would be trapped in the heart. However this was not observed. There was an improved retention but washout was still taking place at an unexpectedly rapid pace.

When the inventors tested the blood, neither the fatty acid, Compound A, nor its precursors were present; however they did find indications in the urine of products from an unexpected alpha oxidation which led them to believe that alpha oxidation was responsible for degradation of the fatty acid as shown in Equations 7 through 12.

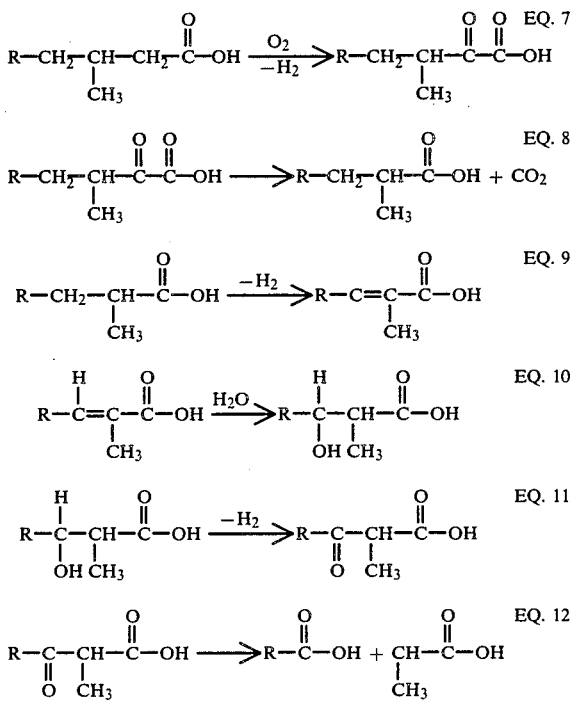

If there is alpha oxidation (EQ. 7) followed by a cleavage of the carbonyl group from the end of the chain (EQ. 8) then the compound is again in condition for beta oxidation (EQ. 11) and subsequent reactions as previously described in Equations 1 through 4.

To test this hypothesis inventors placed a second methyl group at the beta carbon, this time to block subsequent alpha oxidation after initial alpha oxidation. The compound

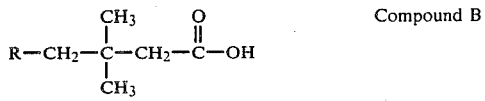

having two methyls at the beta position cannot undergo beta oxidation because there are no free hydrogens to dissociate to give a double bond. The extent to which Compound B might react is an alpha oxidation as shown in Equations 7 and 8 to give the compound

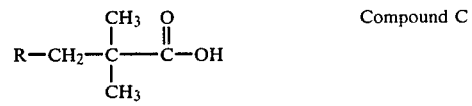

but further oxidation is blocked by the methyl groups. Although placing two methyl groups at the beta carbon limits the reaction to a maximum of one oxidation cycle, moving the dimethyl substitution further from the carboxyl group limits the reaction to the extent that sequential oxidation cannot occur beyond the point at which the dimethyl is at the beta position. When this theory was tested on a fatty acid having dimethyl substitution at the beta carbon when compared with the monomethyl substituted compound the results were impressive. The heart-to-blood ratio improved from 3–4/1 to 10/1 and the t1/2 extended from 45 minutes to 12 hours which is considered indefinite.

EXAMPLE

The synthesis of DMIPP is illustrated in FIG. 1. Dimethylglutaric anhydride (1) was refluxed in methanol to give the ester, which was subsequently chlorinated with thionyl chloride producing an acyl chloride (2). Friedel-Crafts acylation of thiophene (3) with the acyl chloride gave the disubstituted thiophene (4), which was purified by vacuum distillation. Following Wolff-Kishner reduction of (4) and methylation with diazomethane, the thiophene (5b) was acylated in the 5-position by treatment with 6-phenylhexanoyl chloride (6) to give the 2,5-disubstituted thiophene (7). Subsequent Wolff-Kishner reduction then gave the disubstituted thiophene which was ring-opened with sulfur extrusion to give 15-phenyl-3,3-dimethylpentadecanoic acid (9). Iodination was accomplished by thallation in trifluoroacetic acid with thallium(III)trifluoroacetate followed by reflux with potassium iodide. Under these conditions, the para-iodo product (10) is formed with greater than 95% regioselectivity. The overall yield of the substrate (9) from (1) is approximately 20%. Radioiodination of (9) can be conducted on a microscale (0.1 micromole) to give (10) in 60–80% in high specific activity (1–4 Ci/mmol). All these processes are known to persons skilled in the art.

Iodine-125 DMIPP was administered in 6% BSA solution to groups of fasted and fed rats. The animals were killed at time periods varying from 5 min to 8 h and selected tissues and aliquots of blood removed and analyzed in a gamma spectrometer. This new agent showed high myocardial uptake and prolonged retention in the hearts of fasted rats. While BMIPP was washed out at a rate of approximately 40% loss after 60 min., DMIPP exhibited prolonged retention with only approximately 24% loss even after 4 h and it remained measurable up to 12 hours. Introduction of dimethyl branching into the IPP molecule resulted not only in a substantial increase in the myocardial retention but also in a dramatic decrease of radioiodine in the blood resulting in much higher heart:blood ratios. Within 15 min. after injection, the mean heart:blood ratios were greater than 10:1 for DMIPP, in contrast to a 3–4:1 ratio for BMIPP.

The compound was tested on rats but it is believed it would give similar results in other warm-blooded animals. It is mixed with a suitable administering medium in sufficient amounts to give a distinct image and is administered intravenously. Such determinations can be routinely made by persons skilled in the art.

Figure 2:
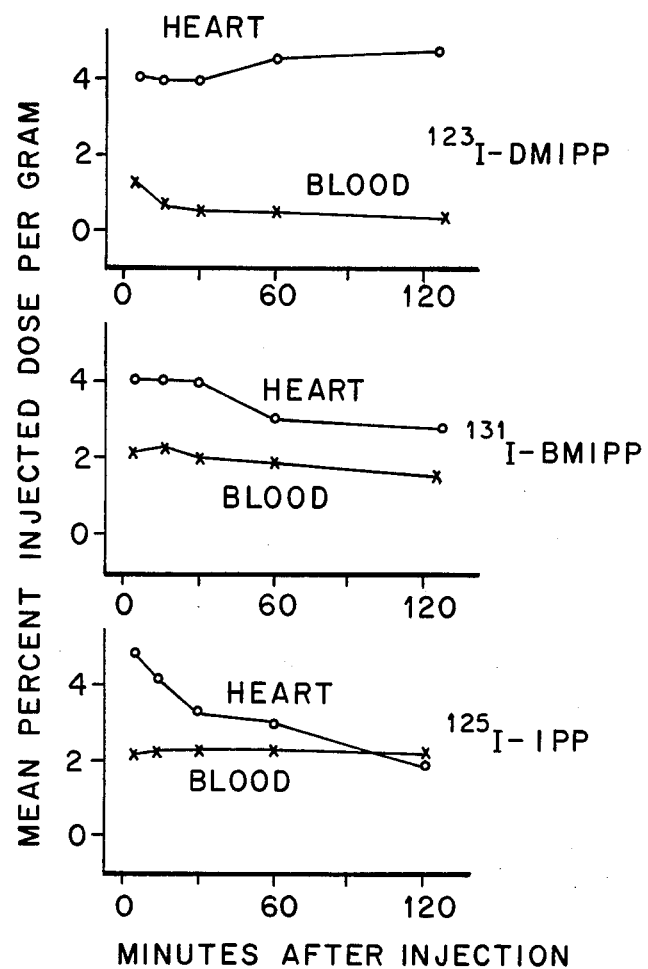
FIG. 2 is a graphic comparison of distributions of [$^{125}$I]IPP, [$^{131}$I]BMIPP and [$^{123}$I]DMIPP in tissues of fasted female Fischer rats as shown in Tables 1 and 2.

The higher heart:blood ratios and significantly increased myocardial retention observed with ($^{125}$I)DMIPP in comparison to the monomethyl (BMIPP) and unbranched (IPP) analogues were further evaluated and confirmed in a triple-label experiment in which a ($^{123}$I)DMIPP/($^{131}$I)BMIPP/($^{125}$I)IPP mixture was administered to fasted rats. The possibility of "competition" between the fatty acids for diffusion into the myocardial cells was felt to be unlikely since the effects of relative BMIPP/IPP mass ratios on biodistribution properties in rats had previously demonstrated an insignificant effect in ratos of up to 6:1. Nevertheless, in the present experiment, the mass of each fatty acid injected was very similar to eliminate any effects of possible synergistic action on myocardial uptake. The details of this experiment are given in Tables 1 and 2. The results of this study are summarized in FIG. 2 and further substantiate the greater retention and higher heart:blood ratios observed earlier with DMIPP. As expected from the large body of information on the myocardial uptake of structurally modified fatty acids available in the literature, the initial uptake or "extraction" phase reflects regional perfusion and is very similar for these three agents. Within a few minutes following injection, however, differences in retention are clearly evident in fasted animals.

TABLE 1

DISTRIBUTION OF RADIOACTIVITY
(% INJECTED DOSE/GRAM OF TISSUE) IN FASTED
RATS AT VARIOUS TIMES AFTER INTRAVENOUS ADMINISTRATION OF
15-(p-[$^{125}$I]IODOPHENYL)-3,3-DIMETHYLPENTADECANOIC ACID (DMIPP)

| Tissue | Time after injection; Percent injected dose/gram (range) | | | | | |
|---|---|---|---|---|---|---|
| | 5 min | 30 min | 1 h | 2 h | 4 h | 8 h |
| Heart | 4.67 | 5.06 | 4.49 | 4.37 | 3.53 | 2.24 |
| | (4.30–5.02) | (4.57–5.42) | (4.12–5.13) | (4.03–4.63) | (3.27–3.85) | (2.03–2.58) |
| Blood | 1.48 | 0.42 | 0.36 | 0.35 | 0.31 | 0.24 |
| | (1.39–1.63) | (0.40–0.45) | (0.35–0.38) | (0.31–0.37) | (0.29–0.32) | (0.21–0.28) |
| Lungs | 2.15 | 1.42 | 1.17 | 1.12 | 0.97 | 0.79 |
| | (2.07–2.22) | (1.27–1.71) | (1.10–1.27) | (0.92–1.31) | (0.92–1.04) | (0.72–0.99) |
| Liver | 7.73 | 7.30 | 6.02 | 5.32 | 3.56 | 2.52 |
| | (7.38–7.92) | (7.00–7.72) | (5.52–6.30) | (4.95–5.65) | (3.44–3.70) | (2.19–2.79) |
| Kidneys | 1.39 | 1.47 | 1.46 | 1.41 | 1.39 | 1.19 |
| | (1.34–1.45) | (1.39–1.53) | (1.43–1.50) | (1.30–1.54) | (1.31–1.58) | (1.14–1.26) |
| Thyroid | 16.7 | 18.5 | 15.8 | 17.9 | 22.9 | 27.8 |
| | (11.9–19.9) | (14.1–24.4) | (14.7–18.2) | (16.9–18.5) | (18.5–28.2) | (23.9–30.2) |
| Mean Heart:Blood | 3:1 | 12:1 | 12.5:1 | 12.6:1 | 11.2:1 | 9.3:1 |

Mean and range values for five (5, 30 and 60 min) or four (2, 4 and 8 h) female Fischer rats. Other tissues that were analyzed include spleen, brain and intestines.

TABLE 2

DISTRIBUTION OF RADIOACTIVITY
(% INJECTED DOSE/ORGAN OF TISSUE) IN FASTED
RATS AT VARIOUS TIMES AFTER INTRAVENOUS ADMINISTRATION OF
15-(p-[$^{125}$I]IODOPHENYL)-3,3-DIMETHYLPENTADECANOIC ACID (DMIPP)

| Tissue | Time after injection; Percent injected dose/organ (range) | | | | | |
|---|---|---|---|---|---|---|
| | 5 min | 30 min | 1 h | 2 h | 4 h | 8 h |
| Heart | 1.95 | 2.09 | 2.24 | 1.99 | 1.56 | 1.05 |
| | (1.81–2.10) | (1.97–2.24) | (2.15–2.35) | (1.92–2.17) | (1.45–1.69) | (0.95–1.14) |
| Blood | 8.47 | 2.30 | 2.41 | 2.24 | 2.04 | 1.59 |
| | (8.07–9.13) | (2.16–2.47) | (2.34–2.56) | (2.11–2.37) | (2.00–2.11) | (1.43–1.71) |
| Lungs | 1.63 | 0.99 | 0.98 | 0.87 | 1.77 | 0.66 |
| | (1.58–1.67) | (0.86–1.19) | (0.92–1.05) | (0.86–1.01) | (0.73–0.80) | (0.58–0.83) |
| Liver | 30.9 | 28.8 | 32.4 | 22.8 | 16.7 | 11.4 |
| | (29.5–32.1) | (27.8–30.7) | (30.2–36.3) | (22.6–23.1) | (16.2–17.0) | (10.4–12.3) |
| Kidneys | 1.45 | 1.49 | 1.51 | 1.62 | 1.58 | 1.34 |
| | (1.38–1.53) | (1.40–1.63) | (1.47–1.61) | (1.54–1.63) | (1.46–1.75) | (1.22–1.47) |
| Thyroid | 0.14 | 0.15 | 0.11 | 0.17 | 0.22 | 0.28 |
| | (0.10–0.17) | (0.12–0.16) | (0.10–0.13) | (0.16–0.18) | (0.19–0.27) | (0.25–0.30) |

Mean and range values for five (5, 30 and 60 min) or four (2, 4 and 8 h) female Fischer rats. Other tissues that were analyzed include spleen, brain and intestines.

Radioiodine labeled DMIPP is the first example of a structurally modified fatty acid with a Te heteroatom which exhibits the unique property of essentially irreversible myocardial retention over the first couple of hours after intravenous administration to unfasted rats. Dimethyl branching was placed at the beta carbon to compare it with the monomethyl branched analogue and because of ease of synthesis. It is believed that dimethyl branching at the alpha carbon would give similar results.

We claim:

1. The compound 15-(p-radiodophenyl)-3,3-dimethyl-pentadecanoic acid.

2. A myocardial imaging agent comprising:
15-(p-radioiodophenyl)-3,3-dimethyl-pentadecanoic acid and a physiologically compatible carrier medium which is suitable for intravenous injection.

* * * * *